United States Patent [19]

Harper et al.

[11] Patent Number: 5,455,344
[45] Date of Patent: Oct. 3, 1995

[54] AGAROSE COMPOSITIONS FOR NUCLEIC ACID SEQUENCING

[75] Inventors: David L. Harper, Rockland; Jonathan H. Morgan, Camden, both of Me.; Samuel Nochumson, Randolph, N.J.; Mikhail V. Ostrovsky, Rockland, Me.; Donald W. Renn, Glen Cove, Me.; William C. Snow, Rockland, Me.

[73] Assignee: FMC Corporation, Philadelphia, Pa.

[21] Appl. No.: 116,662

[22] Filed: Sep. 3, 1993

[51] Int. Cl.$^6$ .......................... C08B 37/00; C08B 37/12; C12N 15/10
[52] U.S. Cl. .................. 536/123.1; 536/25.4; 935/77
[58] Field of Search ........................ 536/1.1, 25.4, 536/123.1; 935/77

[56] References Cited

U.S. PATENT DOCUMENTS

| | | | |
|---|---|---|---|
| 3,766,047 | 10/1973 | Elevitch | 204/299 |
| 3,956,273 | 5/1976 | Guiseley | 260/209 R |
| 4,319,975 | 3/1982 | Cook | 204/180 |
| 4,774,093 | 9/1988 | Provonchee et al. | 424/493 |
| 4,857,163 | 8/1989 | Gurske et al. | 204/299 R |
| 4,983,268 | 1/1991 | Kirkpatrick et al. | 204/182.8 |
| 5,055,517 | 10/1991 | Shorr et al. | 524/813 |
| 5,073,603 | 12/1991 | Ponticello | 525/350 |
| 5,159,049 | 10/1992 | Allen | 524/56 |

FOREIGN PATENT DOCUMENTS

| | | |
|---|---|---|
| 0356960 | 3/1990 | European Pat. Off. . |
| 4248460 | 9/1992 | Japan . |
| WO9302571 | 2/1993 | WIPO . |

OTHER PUBLICATIONS

"Electrophoresis" 10:741–747 (1989) Hoffman et al.
"Sea Notes" (FMC Corp., Winter 1980–1981).
"Nucleic Acids Research", Smith et al. 9:5269–5286 (1981).
"Analytical Biochemistry" 98:358–367 (1979) Locker.
"Nucleic Acids Research" R. Frank et al. 9:4967–4979 (1981).
"Molecular Cloning"—2nd edition, Sambrook, Fritsch & Maniates, Cold Spring Harbor Labroatory Press (1989).
"Sigma Chemical Co.", St. Louis, Mo. pp. 1556–1560, 1993.
"The Agarose Monograph" pub. by FMC Corporation (1988).
"BioProducts Catalog 1994" pub. by FMC Corporation.

*Primary Examiner*—Douglas W. Robinson
*Assistant Examiner*—Gary L. Kunz
*Attorney, Agent, or Firm*—Mark A. Greenfield; Robert L. Andersen

[57] ABSTRACT

A nucleic acid sequencing gel comprising 2 to 10% of a gelling polysaccharide, preferably agarose; a denaturing agent, a non-gelling additive, preferably glycerol, and electrophoretic buffers. This composition is capable of resolving nucleic acid fragments having at least 50 bases and which differ from each other by at least one base.

26 Claims, No Drawings

AGAROSE COMPOSITIONS FOR NUCLEIC ACID SEQUENCING

BACKGROUND OF THE INVENTION

1. Field of the Invention

This invention affords nucleic acid (DNA/RNA) sequencing gel compositions and a method for using same. The composition comprises an aqueous gel of one or more polysaccharides, one or more denaturing agents, one or more optional non-gelling additives, and buffers.

2. Description of Related Art

Techniques for sequencing DNA (deoxyribonucleic acid) were discovered in the late 1970's and have become very important tools in molecular biology. The basic technology for sequencing DNA, and newer methods which may involve other forms of nucleic acid such as RNA (ribonucleic acid), may be divided into two steps for the purpose of this invention. First, a set of single-stranded nucleic fragments is generated. Current techniques in wide use for this step include the well-known methods of Sanger and of Maxam & Gilbert, as well as newer methods such as "cycle sequencing". Second, the fragments produced by any of these techniques are separated by molecular weight by gel electrophoresis. The resulting pattern of "bands" of DNA fragments separated by size is then "read" (interpreted) to determine the nucleotide sequence of the original DNA in the reaction. The original gel medium for performing this separation was the crosslinked polyacrylamide gel, containing high levels of urea to minimize formation of secondary structure in the DNA fragments. There has been very little change in the formulation and method of manufacture of the polyacrylamide gel since the beginning of the technique. Traditional sequencing gels are tedious to make. It would clearly be of use to laboratory researchers to have these complex gels prefabricated, to reduce the labor and uncertainty of making them. However, the traditional gel has proven to have poor storage stability, and cannot in general be kept over about a week, even at 4° C., before suffering loss of resolution. The stabilization of polyacrylamide gels is difficult and tedious, as discussed in U.S. Pat. No. 5,159,049—Allen. Attempts have been made to use other polymers for the sequencing gel—for example, to use substituted acrylamides in place of acrylamide, or to use improved crosslinkers [see U.S. Pat. No. 5,055,517—Schorr, et al.; and EPA 89/115 833.9]; and U.S. Pat. No. 5,073,603—Ponticello discloses oxygen-tolerant methods for making acrylamide gels. However, none of these is known to be available as a storage-stable sequencing gel.

It is essential in DNA sequencing to use a gel which can separate bands having a molecular weight difference of only one nucleotide. This can be an extremely demanding separation. To separate DNA fragments with 100 as compared to 101 bases requires a resolution value of 1%; a more typical requirement is separation of 200 and 201 bases giving a resolution value of 0.5 %; separations in the range 300 to 400 bases giving a resolution value as low as 0.25% are at the limit of present technology with a single loading.

It has been known for decades that agarose forms a very stable gel. Agarose gels can be kept for years with little change in properties, as long as the moisture level is maintained. However, agarose has been considered unsuitable as the primary gel polymer in sequencing gels. One school of thought has believed that agarose is too poorly sieving to give adequate separation in the very demanding DNA sequencing application [see U.S. Pat. No. 4,857,163—Gurske, et al., where acrylamide is "too sieving" for an agarose use; U.S. Pat. No. 4,319,975—Cook, distinguishing uses for agarose as compared to acrylamide; U.S. Pat. No. 3,766,047—Elevitch, noting that agarose can be too difficult to use for "fine resolution" of one protein from another (which is much less demanding than DNA sequencing), and U.S. Pat. No. 5, 159,049—Allen, at col. 1 line 66. Another common perception is that agarose does not form gels in strong urea solutions [see U.S. Pat. No. 4,774,093—Provonchee, et al.; Hoffman, et al., "Electrophoresis" 10:741-747 (1989); "SeaNotes" (FMC Corporation, Winter 1980-81)]. This is not rigorously correct, because Smith et al., in "Nucleic Acids Research" 9:5269 - 5286, (1981) made solutions of 1.75% agarose in 7 M urea and acid citrate buffer (0.025 M citric acid; pH 4.5), chilled them at 4° C. to make them set into gels, and used the gels to separate large RNA molecules by electrophoresis. The gels were run at 4° C. In addition, the low current level (25 mA) at low ionic strength, and consequently long running time (30 hrs.), prevented heat generation during electrophoresis. Of especial interest is that the 7 M urea did not totally remove secondary structure in the RNA; when secondary structure was completely abolished by use of aldehydes, then the RNA separation failed. Also, Locker ["Analyt. Blochem." 98:358-367, (1979)] separated RNA on agarose gels in the presence of 6 M urea and in neutral solution. The gels were cooled to set them, and run at low voltage (100V for a 20 cm gel, compared to 1000 V for a sequencing gel) and hence at a lower temperature than required for sequencing. Locker notes (p. 364) that the RNA secondary structure is not completely removed in these gels, and that they are therefore not useful for determining molecular weight, even though useful for separating different classes of RNA differing widely in molecular weight, such as transfer compared to messenger and cytoplasmic compared to mitochondrial. These uses are similar to the traditional use of agarose gels for separation of double-stranded DNA fragments of moderate size (about 100 to 10,000 base pairs.)

In contrast, in the sequencing of DNA it is essential to abolish all secondary structure in the DNA being analyzed, so that separation is strictly on the basis of molecular size, since otherwise the sequence cannot be read accurately [see R Frank, et al., "Nucleic Acid Research" 9:4967 -4979, (1981)]. In traditional acrylamide gels, complete denaturation of DNA, to optimize resolution, is accomplished by two mechanisms: (1) by running sequencing gels at elevated temperatures; and (2) by incorporation of a high level of urea, which is partially effective in abolishing secondary structure. It may be noted however, that even in acrylamide, "compression zone" regions of DNA with multiple base repeats do not resolve well. Resolution of compressed zones is normally accomplished by using high levels of current and voltage, so that the gels are kept warm by Joule heating. Typical voltages are 1000 –2000V, (with interelectrode spacing of about 50 cm) or over 10 times the voltages normally used to separate RNAs or double-stranded DNA fragments. Acrylamide has been satisfactory for this use because its coherence as a gel is via covalent crosslinks that are not dissolved by heat or denaturants. However, as noted above, acrylamide has serious problems of chemical stability that prevent prolonged storage of pre-cast gels. Other gelling materials have been used to separate nucleic acids [see for example, JP 4-248460], but separation of double-stranded restriction fragments (differing by tens of base pairs) is shown, rather than the single-base resolution needed for sequencing.

It also may be noted that a prominent text in the field ["Molecular Cloning"—2nd ed, by Sambrook, Fritsch & Maniatis, Cold Spring Harbor Laboratory Press, (1989)] in its discussion of Gel Electrophoresis of DNA—Chapter 6, states at 6:36-37: "Polyacrylamide gels are more of a nuisance to prepare and run than agarose gels. ... However, they have three major advantages over agarose gels: (1) Their resolving power is so great that they can separate molecules of DNA whose lengths differ by as little as 0.2% (i.e., 1 bp in 500 bp)...".

SUMMARY OF THE INVENTION

This invention affords a method for nucleic acid (DNA/RNA) sequencing and a gel composition therefor comprising a polysaccharide aqueous gel, an optional non-gelling additives, a denaturing agent, an electrophoretic buffer, water, and optional other components. Also afforded is a dry combination of precursor ingredients for such gel.

The gels according to this invention are distinguished in that they are capable of resolving nucleic acid fragments having at least 50 bases (and which may range up to 400 bases or more) which differ from each other by at least one base.

Useful aqueous gel-forming polysaccharides include: agarose; glucomannan, especially glucomannan derived from konjac; partially deacetylated glucomannan; beta-1,3-glucans including curdian; beta-carrageenan; furcellaran; agar (agar-agar); chemical derivatives of the foregoing; and mixtures thereof. The chemical derivatives should be of a low degree of substitution, preferably less than two substituents per disaccharide unit, and the substituent moieties should be fairly small, especially less than about 200 daltons. The polymers include polysaccharides with reactive groups, which will form irreversible gels, as well as thermoreversible gels which remelt on heating or alternatively on cooling.

Preferred gel-forming polysaccharides include: agar, agarose, allylglycidyl agarose, curdian, hydroxyethyl curdian, konjac glucomannan, and deacetylated konjac glucomannan; of which agarose, allylglycidyl hydroxyethyl curdian, and deacetylated konjac glucomannan are more preferred, and agarose extracted from *Pterocladia* species of seaweed is most preferred.

The amount of gel-forming polysaccharides present is 2 to 10% [w/w] based on the total weight of the composition, 2 to 8% being preferred, 3 to 6% being most preferred.

Useful optional non-gelling additives include: glycerol, other glycols and polyglycols having four or fewer carbon atoms, dextran, locust bean gum, and highly degraded (depolymerized) agarose. Preferred nongelling additives include: glycerol, ethylene glycol, erythritol and locust bean gum, of which glycerol and erythritol are more preferred, and glycerol is most preferred.

The total amount of non-gelling additives present is 0 to 50% [w/w] based on the total weight of the composition, 2 to 30% being preferred, 5 to 20% being most preferred.

Useful denaturing agents include: urea; $C_{1-6}$ alkyl urea; biuret; $C_{1-6}$ alkyl monoaldehydes and dialdehydes, preferably glyoxal, formaldehyde or glutaraldehyde; formamide and $C_{1-6}$ alkyl formamide; dimethylsulfoxide (DMSO); pyrrolidinone and $C_{1-6}$ alkyl pyrrolidinones; $C_{2-4}$ glycols; and mixtures thereof. Preferred denaturing agents include: urea, formamide, dimethylformamide, and dimethylsulfoxide (DMSO), of which urea, formamide and dimethylformamide, are more preferred, and urea is most preferred. The total denaturant concentration can be 2 to 95 wt %, preferably 10 to 70 wt %, most preferably 12 to 60 wt %, all weights based on the total composition.

Stated otherwise, the amount of denaturing agents present is 1 to 8 M (molar) for urea or other denaturing agent which is a solid at room temperature, with 2 to 6 M being preferred, and 4 to 5 M being most preferred. Liquid denaturants, typically water-miscible organic chemicals such as DMSO, formamides and alkylformamides, are present at 5 to 95% w/w based on the total weight of the composition, 20 to 50% being preferred, 25 to 40% being most preferred. The most preferred denaturant mixture further depends on the polysaccharide gel, being 4–5 M urea for agarose, 4–8 M urea for allylglycidyl agarose and hydroxyethyl curdlan, while mixtures of urea and formamide are preferred for curdlan, and mixtures of urea, DMSO and/or 1-methyl-2-pyrrolidinone are preferred for deacetylated konjac. Especially effective denaturant combinations are:

Native Curdian (non-derivatized)
a) 6 to 8.5M urea alone
b) up to 100% denaturing organic liquid (preferably formamide)
c) 2.8M urea to 8.5M with up to 100% solvent Hydroxyethylated Curdian
a) 0.5 to 8M urea with 20 to 90% liquid denaturant
b) 4 to 6 M urea alone Deacetylated Konjac Glucomannan (DAcK)
a) 4 to 8M urea with 9 to 25% DMSO or 1-methyl-2-pyrrolidinone Useful electrophoretic buffers include all those that are known as effective in electrophoretic systems. Of particular use in connection with the sequencing gels of this invention are: tris-borate-EDTA (TBE), tris-phosphate-EDTA, tris-taurine-EDTA, and tris-acetate-EDTA, preferably tris-borate-EDTA or tris-acetate-EDTA, more preferably tris-borate-EDTA, most preferably TBE at the level of "0.5 X", or about 45 mM tds, 45 mM borate, 1 mM EDTA, pH 8.3. Other useful buffers include carbonate, glycine, and "Good's Buffers" and related zwitterionic compounds. A listing of such buffers can be found in supply catalogs, such as that of Sigma Chemical Company, St. Louis, MO, U.S.A.; pages 1556–1560, 1993 edition.

The concentration of buffer can be any level known in the art, and is subject to the same set of tradeoffs as in any other electrophoresis gel, namely: higher concentrations are better for buffering of long runs, but lower concentrations are preferable for minimizing Joule heating and thereby accelerating gel runs at fixed voltage and/or maximum heating level. A useful level for the polysacchadde gel systems of this invention is between 10 and 200 mM of cation or anion, whichever is less; with 20 to 100 mM being preferred, 30 to 60 mM being more preferred, and about 50 mM being most preferred. The presence of EDTA (as the edetate anion, where EDTA and edetate refer to ethylenediaminetetraacetic acid) is useful to prevent DNA hydrolysis, and as a bacteriostat, with 0.1 to 5 mM being useful, 0.2 to 2 mM being preferred, and 1 mM being most preferred. The total weight of buffer salts in the inventive composition is thus 0.2 to 6 wt %, preferably 0.3 to 5 wt %, most preferably 0.4 to 4 wt % of the total composition.

The pH can be any which is suitable for electrophoretic separation of nucleic acids. In principle, this includes the range of pH 2 to 11. In practice, neutral to mildly alkaline buffers (pH 6.8 to 10) are preferred, to avoid the possibility of depurination or of hydrolysis of the nucleic acid. More preferred pH ranges are 7.5 to 9, and especially preferred pH ranges are 8.2 to 8.6.

A particularly preferred sequencing gel composition of this invention is 5.5% *Pterocladia* agarose with 4.4 M urea and 5% glycerol in 0.5 X TBE (tris-borate -EDTA) buffer. It has the advantages of non-toxicity and of improved storage stability.

In addition to being capable of use in nucleic acid sequencing, and to having a resolution value at least as high as 1% (that is, being capable of resolving between one base where the nucleic acid fragments have 100 bases or less), one of the very important criteria for the compositions of this invention is that they are stable upon storage, and another very important criteria is that the sequencing gel is not a polyacrylamide.

The sequencing method of this invention is essentially the same as that used at present for sequencing, with the critically important difference that the inventive compositions and not polyacrylamides are employed as the sequencing gels.

Moreover, as an ancillary benefit, gel formulations of this invention are also suitable for performing electrophoresis separations requiring similar or lesser resolving power than that required for sequencing, such as RNA transcription analysis, "footprinting" and other protection assays, and DNA-protein interaction assays.

DETAILED DESCRIPTION OF THE INVENTION

Other than in the operating examples, or where otherwise indicated, all numbers expressing quantities of ingredients, parameters, or reaction conditions used herein am to be understood as modified in all instances by the term "about".

Sequencing gels were prepared of acrylamide and of experimental materials according to this invention. All gels contain buffer; this was normally "0.5X TBE", a 1:1 dilution in water of the TBE buffer of Sambrook et al.(op. cit.) The 1X solution contains 89 mM Tris ("tris(hydroxymethyl)aminomethane"; 2-amino-2-hydroxymethyl-1,3-propanediol), 89 mM boric acid, and 2 mM EDTA; pH 8.4. Gels were cast between parallel glass plates separated by standard spacers, which were normally 0.4 mm thick. The high viscosity of the polysaccharide solutions used in this invention may indicate the preference of alternative methods of casting, compared to classical polyacrylamide gels. The method of casting is not itself part of the invention, and any casting method which produces a thin and uniform film of gelled polysaccharide is useful in this procedure. However, simply pouring the dissolved polysaccharide mixture between the apposed plates of the casting cassette, as is done with polyacrylamide, is tedious and impractical, even at elevated temperatures. A better method is the injection of the mixture between the plates by filling a syringe with the mixture, and forcing the mixture between the plates by pressure on the syringe. This technique is improved by using a caulking gun, or similar pressure-amplifying device, to apply pressure to the syringe. Since the narrow-gauge needle needed to fit between the plates of the cassette is a major source of backpressure, an even better method is to drill a small (about 5 mm diameter) hole in one of the glass plates of the casting cassette; affix to the hole an adaptor capable of receiving a syringe, such as a disposable luer adaptor; and forcing the mixture in through the resulting port. This is the best method for making a gel of the preferred composition, which contains 5.5% high-molecular weight agarose. The port is sealed with tape after casting, and, if formed near the bottom of the cassette, does not noticeably disturb the uniformity of the electrophoretic separation. Other methods known in the art may be best for high volume production, such as extrusion, calendaring, and related techniques which have not yet been attempted but are contemplated.

In some experiments support films for the gels were used (GeiBond®, or GeiBond PAG, products of FMC Corporation, BioProducts Group, Rockland, Maine). Sequencing reactions were performed using the Sanger dideoxy technique and labelled with the isotope S-35, using standard kits for this purpose (available from U.S. Biochemical Corp, and others). Aliquots of sequencing reactions were frozen at $-70°$ C. for up to 3 weeks before analysis by electrophoresis. Gels were normally pre-run for about 30 min. at about 1500V before applying sample. Sequencing reactions were separated by electrophoresis run at a fixed voltage (typically 1000 to 2000V, most commonly at 1400–1800V), or at a fixed power level giving about 1500V in chambers of the usual length for sequencing, having an interelectrode spacing of 50 cm (45–60 cm) and an operative length of 40–43 cm. Temperatures of gels during electrophoresis were measured indirectly using the temperature at the outside of the glass plate. Completion of the electrophoretic run was determined by the migration of a tracking dye such as bromphenol blue (Sambrook, op. cit., p. 6.12). On completion, gels were removed from their cassettes, fixed and washed in 1 liter of fixing solution (acetic acid/methanol/water mixture, 1:1:8 by volume) for 1 hour total with gentle rocking, and dried on a standard gel dryer at 60° C. Acrylamide gels were dried onto paper, with a plastic-wrap cover, while agarose and other carbohydrate gels were dried onto Gelbond support film with a paper cover which was peeled off afterward. After drying, separated DNA bands on the gels were detected by autoradiography. Sequencing quality was evaluated by determining the readability of the first 200 bases in acrylamide gels, and in gels of the experimental materials according to this invention, on which the same sequence had been run; and also on the ability of gels to separate runs of 4 or more guanosine bases at 150 bases and above in the sequence being read. It was found to be most practical and adequately reliable to evaluate results qualitatively by rating the gels on the following scale:

| | |
|---|---|
| 5 | (excellent) |
| 4 | (good) |
| 3 | (fair) |
| 2 | (poor) |
| 1 | (very poor) |
| 0 | (completely ineffective - failure) |

The materials mentioned were of ordinary reagent grade, except that urea and formamide were deionized and sold as "suitable for sequencing", or similar grade. Agaroses, locust bean gum, and konjac glucomannans are available from FMC Corporation, BioProducts Group, Rockland, Maine, U.S.A. or FMC Litex S/A, Vallensbaek Strand, Denmark). Select agar was obtained from Sigma Chemical (# A-5054). Curdian was obtained from Takeda Chemical Company, Japan; it was purified by washing with 1% $NaHCO_3$ before use. Details of the experimental procedures are not critical to the invention, and similar techniques from the literature can be substituted.

The detailed method for making the gels is not a part of this invention. Agarose is prepared by conventional procedures. Powder is dispersed in buffered solution, such as boiling on a hot plate or in a microwave oven, for at least 4 minutes, typically 7–10 minutes, and for up to 20 minutes. Denaturing agents and non-gelling additives are typically added after completion of boiling, but may be added before boiling where the ingredients are not volatile. After all additions are complete, the solution is weighed and water added to restore final weight if required. The solution is tempered to about 70° C., and is held at that temperature for up to 8 hours. After casting, gel-filled cassettes are normally placed directly at 4° C. (refrigerator or cold room) to set them, but may optionally be held at 70° C., or at other temperatures such as room temperature (15–25° C.) to allow tempering of the mixture in the cassette. It is important that the casting operation be conducted at temperatures above the gelation temperature of the agarose/urea mixture.

The non-agarose systems have somewhat different requirements, which are characteristic of the properties of the polymers and are known to those familiar with those polymers. As examples, allyiglycidyl agarose is dissolved by heating to ensure complete solution, but is gelled essentially at room temperature by addition of crosslinking agents just before casting. These solutions can only be held until the crosslinkers are added. Hydroxyethyl curdlan behaves similarly to agarose in most respects. Konjac glucomannan is heated to dissolve it, held at room temperature while other ingredients are added, and then gelled by heating of the filled cassette, as is known for konjac gels in general.

EXAMPLES

Procedure for Examples 1 and 2:

A sequencing gel was made of agarose as follows: 1.5 grams (g) of agarose extracted from *Pterocladia* species (available from FMC) was dissolved by boiling for at least 4 minutes, but not more than 20 minutes, in 25 milliliters (mL) of an aqueous solution containing 1X TBE buffer and optionally 1–20% glycerol (w/w) as below described. After completion of boiling, 12.01 g of urea was added and the solution was stirred while maintaining its temperature at 70° C. or above 0 until the urea was dissolved. The solution was then tared to a total weight of 50 g with distilled water. Then about half of the agarose solution was injected between parallel glass plates (16.5×40 cm) which were separated by 0.4 mm spacers. For this injection, the agarose solution was placed in a pre-warmed syringe at 55×60° C. When the viscosity of the agarose was high, an ordinary caulking gun was used to force the agarose solution from the syringe. The plate assembly was prewarmed to 55° C., and after injection of agarose the filled cassette was maintained at 70° C. for 60 min. Then the cassette was optionally held at room temperature (15– 20° C.) for 60 minutes. Finally, the filled cassette was refrigerated at 4° C. for at least 30 min., and preferably for 60 min. to overnight, to induce complete gelling of the agarose. This formulation contains 3% agarose, nominal 0.5X TBE buffer, nominal 4 M urea denaturing agent, and some glycerol; such a composition is abbreviated as "3% agarose/4 M urea/0.5X TBE/x % glycerol", but it should be noted that the actual concentrations per unit volume of the constituents (agarose or other polysaccharide, buffer, urea, other additive) are about 10% higher than the nominal values, because the solution is made up per unit weight. All concentrations of buffer and urea used with polysaccharide gels described here are nominal, unless otherwise stated. Variants of this formula were made by variations in the amounts of the ingredients listed above, dissolved by similar procedures.

Procedure for Examples 3 and 4:

A prior art control gel (6% PAN8M urea/0.5X TBE) was made of polyacrylamide with the following composition: 2.85g acrylamide;0.15 g methylenebisacrylamide; 24.02 g urea; 5 ml 5X TBE buffer; and water to 50 ml. To the 50 ml solution, 0.3 ml of 10% ammonium persulfate was added, and as a last step, 0.05 ml of TEMED (tetramethyl ethylenediamine) was added to initiate the polymerization. The mixture was poured or injected between glass plates as above, and allowed to polymerize at least overnight before use.

The agarose and control (polyacrylamide) gels were run under two voltage conditions on an apparatus with inter-electrode spacing of 55 cm, and the overall quality of the sequencing was evaluated by inspection and by the number of readable bands. The results are shown in Table 1:

TABLE 1

| EXAMPLE # | GEL | VOLTAGE | RESULT |
| --- | --- | --- | --- |
| 1 | Agarose | 1400 V | excellent (5) |
| 2 | Agarose | 2000 V | failed (0) |
| 3 | Acrylamide | 1400 V | excellent (5) |
| 4 | Acrylamide | 2000 V | excellent (5) |

It was found that at high running voltages, such as 2,000V, the agarose gels partially melted, giving poor or no resolution. However, when run under optimal conditions, such as 1400V, agarose gels gave results equivalent to acrylamide gels.

EXAMPLES 5–13: EFFECT OF AGAROSE CONCENTRATION ON SEQUENCING.

Agarose gels were made as described above, containing 4M urea, 0.5 X TBE, and varied concentrations of glycerol, and various concentrations of agarose (derived from *Pterocladia*). Gels were pre-run, typically at 1500V for ½ h. After sample loading, gels were run at ≦1750 V at ≦53°, for about 120 min. or until the bromphenol blue tracking dye exited from the gel. The quality of the separated DNA sequences was evaluated. Data are tabulated in Table 2.

TABLE 2

| EXAMPLE | AGAROSE [%] | GLYCEROL [%] | RESULT |
| --- | --- | --- | --- |
| 5 | 1 | 20 | Very Poor (1) |
| 6 | 2 | 20 | Fair (3) |
| 7 | 3 | 0 | Good (4) |
| 8 | 3 | 20 | Good (4) |
| 9 | 4 | 20 | Good (4) |
| 10 | 5.5 | 5 | Excellent (5) |
| 11 | 6 | 0 | Fair (3) |
| 12 | 6.1 | 5 | Good (4) |
| 13 | 7.0 | 5 | Fair (3) |

From the above data, it is clear that gelling polysaccharide (agarose) concentrations ranging from about 2% to at least 7% are suitable, and concentrations of 3%–6% are best. The presence of an optional non-gelling additive (glycerol) appears less important than the gelling polysaccharide concentration, but clearly influences the results.

EXAMPLES 14–21:

Agarose gels were prepared as above, in 3% agarose, 4M urea, and 0.5% TBE. The concentration of glycerol was varied, as shown in Table 3.

TABLE 3

INFLUENCE OF GLYCEROL CONCENTRATION

| EXAMPLE NO. | GLYCEROL [%] | RESULT |
|---|---|---|
| 14 | 0 | Good (4) |
| 15 | 1 | Good (4+) |
| 16 | 2.5 | Good (4+) |
| 17 | 5 | Excellent (5) |
| 18 | 20 | Excellent (5) |
| 19 | 27 | Good (4–) |
| 20 | 35 | Good (4–) |
| 21 | 50 | Fair (3) |

From the above examples, it was determined that sequencing was possible in the presence or absence of glycerol in the system, but an addition of 5 to 20% glycerol gave the best results. Within this range, the system with 5% glycerol had the best sharpness, but the system with 20% glycerol gave better band spacing.

EXAMPLES 22–30: EFFECT OF DNA DENATURING AGENTS, BUFFER CONCENTRATION, AND GLYCEROL IN COMBINATION.

A gelling polysaccharide (agarose) at a gel concentration of 3% w/w in 0.5X TBE was mixed with various combinations of a DNA denaturing agent (urea) and non-gelling additive (glycerol), and evaluated for its effectiveness in sequencing. The results are shown in Table 4.

TABLE 4

INFLUENCE OF UREA, GLYCEROL, AND TBE CONCENTRATION.

| EXAMPLE | TBE | UREA [M] | GLYCEROL [%] | AGAROSE | RESULT |
|---|---|---|---|---|---|
| 22 | 0.5X | 4 | 20 | Pterocladia | excellent (5) |
| 23 | 0.5X | 4 | 0 | Pterocladia | good (4) |
| 24 | 0.5X | 0 | 20 | Pterocladia | fair (3) |
| 25 | 0.5X | 0 | 0 | Pterocladia | failure (0) |
| 26 | 0.1X | 4 | 20 | Pterocladia | good (4) |
| 27 | 0.1X | 0 | 20 | Pterocladia | poor (2) |
| 28 | 0.1X | 4 | 0 | Pterocladia | poor (2) |
| 29 | 0.5X | 6 | 0 | SeaKem Gold | fair (3) |
| 30 | 0.5X | 4 | 0 | SeaKem Gold | good (4) |

Performance was best at 4M to 6M (nominal) denaturant (urea). A buffer present at 0.5X (nominal) was better than at 0.1X. Confirming previously discussed examples, a 20% w/w additive (glycerol) content was better than the absence of an additive.

EXAMPLES 31–41: THE EFFECT OF DIFFERENT TYPES AND CONCENTRATIONS OF BUFFER

The results are shown in table 5. All gels were 3% w/w gelling polysaccharide (Pterocladia-derived agarose) and run in 4M nominal denaturant (urea).

TABLE 5

INFLUENCE OF BUFFER TYPE OR CONCENTRATION

| EXAMPLE | GLYCEROL [%] | TBE | TAURINE | UREA | RESULT (TTE) |
|---|---|---|---|---|---|
| 31 | 0 | 0 | 40 | 4M | Good (4) |
| 32 | 0 | 0.25x | 0 | 4M | Fair (3) |
| 33 | 0 | 0.125x | 0 | 4M | Fair (3) |
| 34 | 0 | 0.1x | 0 | 4M | Poor (2) |
| 35 | 2.5 | 1.0x | 0 | 4M | Good (4) |
| 36 | 2.5 | 0.5x | 0 | 4M | Good (4) |
| 37 | 2.5 | 0.1x | 0 | 4M | Fair (3) |
| 38 | 2.5 | 0.1x | 0 | 4M | Fair (3) |
| 39 | 20 | 1.0x | 0 | 4M | Good (4) |
| 40 | 20 | 0.5x | 0 | 4M | Excellent (5) |
| 41 | 20 | 0.1x | 0 | 4M | Good (4) |

The 0.5X level of TBE appears to be the optimal buffer under all glycerol levels examined. Adequate (but less than optimal) functionality was seen with TBE buffer concentrations ranging from 0.125X to 1X, and with 1X TTE (in which the buffer ion taurine replaced the borate ion in the formulation.)

EXAMPLES 42–63: EFFECT OF OTHER ADDITIVES

Gels containing 3% gelling polysaccharide (Pterocladia-derived agarose), 4M denaturant (urea), and 0.5X buffer (TBE) were made containing a variety of additives (all listed as % w/w), and their effect on sequencing quality was determined. Results are shown in Table 6.

TABLE 6

| EXAMPLE | GLYCEROL [%] | ADDITIVE | CONC'N [%] | RESULT [%] |
|---|---|---|---|---|
| 42 | 0 | None | 0 | Good (4) |
| 43 | 0 | Erythritol | 2.5 | Excellent (5) |
| 44 | 0 | Erythritol | 10.0 | Good (4) |
| 45 | 0 | Erythritol | 20.0 | Good (4) |
| 46 | 0 | None | 0 | Good (4) |
| 47 | 0 | Erythritol | 2.5 | Very good (5) |
| 48 | 5.0 | Glycerol | 0 | Excellent (5) |
| 49 | 5.0 | Erythritol | 2.5 | Very good (5) |
| 50 | 5.0 | Erythritol | 2.5 | Very good (5) |
| 51 | 0 | L-Arabitol | 2.5 | Poor (2) |
| 52 | 0 | D-Arabitol | 2.5 | Poor (2) |
| 53 | 0 | Pentaerythritol | 2.5 | Fair (3) |
| 54 | 0 | SeaKem-LE* | 1.0 | Good (4) |
| 55 | 0 | PVA 10KD, 14KD | 1.0 | Very poor (1) |
| 56 | 1.0 | None | 0 | Good (4+) |
| 57 | 1.0 | Hydroxy ethyl cellulose | 0.5 | Very poor (1) |
| 58 | 2.5 | None | 0 | Good (4+) |
| 59 | 2.5 | Ethylene glycol | 1.0 | Good (4) |
| 60 | 2.5 | Ethylene glycol | 2.5 | Good (4) |
| 61 | 2.5 | Ethylene glycol | 5.0 | Good (4) |
| 62 | 2.5 | PEG M.W 200 | 0.2 | Fair (3) |
| 63 | 2.5 | Sorbitol | 2.5 | Poor (1–2) |

*300K.Rad

The above data shows that the addition of polyols of low molecular weight such as ethylene glycol ($C_2$) or erythritol ($C_4$) gives results similar to the addition of glycerol. $C_5$ polyols (arabitol, pentaerythritol); $C_6$ polyols (sorbitol); or polymeric polyols such as polyvinyl alcohol (PVA); hydroxyethylcellulose; and low molecular weight polyethylene glycol (PEG 200); were not as effective. However, low-molecular weight partially depolymerized agarose (SeaKem LE 300 KR) was an effective additive. (The low molecular weight agarose was made by irradiating a commercial agarose, SeaKem® LE, (a product of FMC Corporation, BioProducts Group, Rockland, Maine, U.S.A.) with 300 kiloRads of gamma rays from a cobalt source.)

EXAMPLES 64–69: DIFFERENT GEL-FORMING POLYSACCHARIDES

Gels were made of various types of gel-forming polysaccharide (agarose). All contained 4M urea, 0.5X TBE, and 3% w/w of gel-forming agarose. The agarose types are: XLE, *Pterocladia* agarose (as above) fractionated with alcohol (see U.S Pat. No. 4,983,268—Kirkpatrick, et al.); HSB, a standard commercial agarose made from *Gracilaria* seaweeds; SeaKem® Gold agarose, a commercial *Gelidium* agarose made by fractionation (a product of FMC Corporation); *Pterocladia*, the parent agarose to the above XLE. The results am summarized below in Table 7.

TABLE 7

| EXAMPLE | AGAROSE | GLYCEROL (%) | RESULT |
|---|---|---|---|
| 64 | XLE | 0 | good (4−) |
| 65 | HSB | 0 | good (4−) |
| 66 | SeaKem-Gold | 0 | good (4) |
| 67 | SeaKem-Gold | 5 | good (4) |
| 68 | Pterocladia | 5 | excellent (5) |
| 69 | XLE | 5 | good (4) |

All agaroses tested were functional; the optimum system appears to be *Pterocladia* agarose containing 5% glycerol, but SeaKem Gold agarose and fractionated *Pterocladia* are also suitable.

At higher gel concentrations, such as 5–6%, the differences between these agaroses was not significant in terms of performance rating, which was generally 5 (excellent); but *pterocladia* continued to be somewhat preferred because it has a lower viscosity than the other agaroses.

EXAMPLES 70–72: EFFECTS OF LOCUST BEAN GUM ADDITION

SeaKem Gold agarose, as in example 7, was mixed in varying ratios with clarified locust bean gum (cLBG "D-X"; a product of FMC Corporation, Philadelphia, Pa., U.S.A., which had been irradiated(10 KGy) to reduce its viscosity.) All gels were run in 4M urea/1X TBE. Results are shown in Table 8.

TABLE 8

EFFECT OF LOCUST BEAN GUM

| EXAMPLE | AGAROSE (%) | CLBG (%) | TBE | GLYCEROL | RESULTS |
|---|---|---|---|---|---|
| 70 | 1.0 | 1.5 | 1x | 2 | Fair (3) |
| 71 | 1.5 | 1.5 | 0.5x | 10 | Poor (2) |
| 72 | 1.5 | 1.5 | 0.25x | 0 | Poor (2) |

The agarose/cLBG mixtures had a highly viscous, honey-like consistency, despite the lowering of the cLBG molecular weight by irradiation. The gels had some ability to perform sequencing, but were distinctly inferior to the preferred formulations of the inventive composition.

EXAMPLES 73–80: OTHER GELLING POLYSACCHARIDES

A variety of materials and mixtures containing predominantly materials gelling by different mechanisms than agarose were tested. Acrylaide® crosslinker, a solution of allylglycidylagarose (a product of FMC Corporation, BioProducts Group, Rockland, Me., U.S.A.) was polymerized by mixing 25 ml of 1 X TBE, 2.5 g of glycerol, 1.5 g of allylglycidylagarose, and 10 ml of distilled deionized water (DD water) in a 250 ml Erlenmeyer flask; boiling for several minutes in a microwave oven; replacing any water lost by evaporation; adding 12.01 g urea and swirling to dissolve; and adjusting the weight to 50 g with DD water. To polymerize the mixture, 250 µl of 10% ammonium persulfate and 25 µl of TEMED (tetramethylethlyenediamine) were added, and the mixture was immediately poured into a cassette, heated at 55° C. for one hour, and allowed to polymerize overnight at room temperature. Gels of 3% concentration gave useful sequencing compositions.

Gels of polyvinyl alcohol (PVA), which was weakly complexed and crosslinked by borate in the buffer, were entirely ineffective. A mixture of agarose, PVA and PEG was ineffective. Agar was an acceptable gelling polysaccharide for the inventive composition, although it is less effective than agarose. Agar's utility was decreased by the addition of the nongelling additive glycerol.

TABLE 9

OTHER GELLING POLYSACCHARIDES

| EXAMPLE | INGREDIENT & AMOUNT | RESULT |
|---|---|---|
| 73 | 4% allylglycidyl agarose<br>4M urea - 0.5X TBE | Fair (3) |
| 74 | 3% allylglycidyl agarose<br>4M urea - 0.5X TBE | Fair (3) |
| 75 | 2% allylglycidyl agarose<br>4M urea - 0.5X TBE | Good (4) |
| 76 | 6.67% PVA (MW = 88000)<br>0.3X TBE - 2.7M urea | Ineffective (0) |
| 77 | 5% PVA (MW = 88000)<br>0.5X TBE - 4M urea | Ineffective (0) |
| 78 | 0.55% Pterocladia agarose<br>3.11% PVA (MW = 88000)<br>2.22% PEG (MW = 3350)<br>19.4% Formamide<br>0.17% Borate | Ineffective (0) |
| 79 | 3% Select Agar<br>0.5X TBE - 4M urea | Poor (2) |
| 80 | 3% Select Agar<br>0.5X TBE - 4M urea -<br>20% glycerol | Very Poor (1) |

EXAMPLES 81–87: SEQUENCING SYSTEMS CONTAINING KONJAC & CURDLAN

Curdlan is a linear beta-1,3-polyglucan which can form gels in aqueous solutions [see U.S. Pat. No. 4,774,093—Provonchee, et al.]. Konjac is the common name for a glucomannan extracted from konjac tubers, and is sold by FMC Corporation under the trademark Nutricol®. It is known to form gels in aqueous solution on heating, especially in alkaline solutions.

In the following examples and information, polysaccharide solutions are weight/volume, and molarities and buffer concentrations are exact.

To make a 4% konjac gel, 5.12 g deacetylated clarified konjac (DAcK) (see preparation below) was suspended in 100 ml of a buffer containing 6.40 M urea in 1.28 X TAE buffer (1.0 X TAE is defined in Sambrook, op. cit.). A 3% DAcK composition was also prepared and contained 0.25% SeaKem Gold agarose (0.32 g). The samples were gently heated until dissolved and then allowed to cool to room temperature. 25.5 ml DMSO was then slowly added and after completion, 2.6 ml of 1M boric acid was added with vigorous stirring. The final composition was then 4% DAcK or 3% DAcK/0.25% agarose in 5M urea, 20% DMSO, 1X TAE and 20 mM borate. These sols were then cast into the appropriate cassette and sealed. The entire cassette was then placed in a forced air oven at 83° C. for 60 minutes. The gel was removed and immediately pre-electrophoresed according to normal procedure. Results are shown below in Table 10. In summary, deacetylated konjac was effective, in the presence of 20% DMSO. Other formulations tested were effective. In particular, mixtures of agarose with konjac and with curdlan were effective, even when the agarose was present at only 0.25%.

Deacetylated konjac (DAcK) was prepared from clarified konjac powder, which itself was prepared according to Snow and Renn, laid-open PCT application WO 93/02571. This clarified material was then deacetylated in the following manner:

Clarified konjac powder was suspended in about ten times its weight of 60% isopropanol/40% water containing 1M KOH and incubated for about 1 hr at 55° C. The powder slurry was washed three times with water (5–8 times by weight) by decantation, acidified to pH 5.5 with HCl, washed with water to neutrality, dnsed with 6 weights of 83% isopropanol, and dried, yielding DAcK powder.

The hydroxyethyl curdlans used in these experiments were prepared in a manner similar to that described for hydroxyethyl agarose in example 3 of U.S. Pat. No. 3,956,273—Guiseley. The exception to that procedure was that the alkaline solution was not neutralized directly but was instead precipitated in acidified 2-propanol. The volumes of 2-chloroethanol used in the various derivatizations of 25 g aliquots of purified curdlan ranged from 1.25 ml to 30 ml.; 15 to 20 ml (0.25–0.30 mol chloroethanol per 25 g curdlan) were used for the materials in the examples below. Hydroxyethyl curdlan was handled similarly to agarose in gel preparation.

TAE buffer (1 X) is 40 mM tds, 40 mM acetate, 0.1 mM EDTA, pH 8.2. Buffer and urea concentrations in these examples are actual, rather than "nominal" as defined above.

EXAMPLE 86: 3% (W/V) HYDROXYETHYL CURDLAN IN 6M UREN0.5X TBE:

To 50 ml of 6M urea/0.5x TBE, 1.5 g of hydroxyethylated curdlan was suspended. The preparation was stirred for approximately 10 minutes at room temperature. The sample was then transferred to a boiling water bath for 7 minutes until dissolved, maximum sol temperature was 85° . The solution was transferred to a pre-heated (70° CC) 60 cc syringe in preparation for casting. The 0.4 mm×16×42 cm cassette, containing GelBond®, was pre-heated 30 minutes at 70° C. The sol was cast without incident and stored at 4° C. for 21 hours/40 minutes prior to electrophoresis.

EXAMPLE 87: 4% (W/V) CURDLAN IN 7M UREA 40% FORMAMIDE/0.5X TBE:

To 50 ml of 7M urea/40% formamide/0.5X TBE, 2.0 g of purified curdlan (gamma irradiated @600 Kraals) was suspended at room temperature. The beaker was immediately placed on a fully pre-heated hotplate and stirred approximately 10 minutes. The sol was transferred to a pre-heated 60 cc syringe. An empty 0.4 mmx 16×42 cm cassette was pre-heated for 60 minutes at 70° C. The sol was cast without incident and stored at 4° C. for 20 hours/5 minutes prior to electrophoresis.

(Note: in these experiments, urea was from Fluka, #3206961/1 1092; formamide was from J. T. Baker, "ultrapure, bioreagent" #F36602; TBE was prepared from 10×concentrate, BRL #DBK 601)

TABLE 10

SEQUENCING SYSTEMS CONTAINING KONJAC AND CURDLAN

| EXAMPLE | COMPOSITION | RESULT |
|---|---|---|
| 81 | 3% hydroxyethyl curdlan, 0.25% SeaKem Gold agarose, 7M urea, 20% DMSO, 1X TBE | fair (3) |
| 82 | 4% deacetylated konjac, 5M urea, 20% DMSO, 0.5X TAE buffer plus 20 mM borate; 1 mm thick gel | fair (3) |
| 83 | as per example 82, except 0.4 mm thick | good (4) |
| 84 | repeat of 84, with sample wells made from 1% agarose (SeaKem LE) | failed (0) |
| 85 | 3% Pterocladia agarose, 0.5% deacetylated konjac, 4M urea, 5X TBE | good (4) |
| 86 | 3% (w/v) hydroxyethyl curdlan, 6M urea, 0.5X TBE | poor (2) |
| 87 | 4% (w/v) curdlan, 7M urea, 40% formamide | poor (2) |

The results of Table 10 demonstrate that glucomannan (from konjac), curdlan, hydroxyethylated curdlan, and mixtures of these with agarose are useful in sequencing.

We claim:

1. An aqueous nucleic acid sequencing gel consisting essentially of:

[a] 2 to 10 wt % of one or more gelling polysaccharides selected from the group consisting of agarose, deacetylated konjac glucomannan, and hydroxyethyl curdlan;

[b] 2 to 95 wt % of one or more denaturing agents;

[c] 0 to 50 wt % of one or more non-gelling additives;

[d] 0.2 to 6 wt % of one or more electrophoretic buffers; and

[e] water sufficient to 100 wt %;

wherein the gel is capable of resolving nucleic acid fragments having at least 50 bases which differ from each other by at least one base.

2. A dry combination of nucleic acid sequencing aqueous gel precursor ingredients consisting essentially of:

[a] 2 to 10 wt % of one or more gelling polysaccharides selected from the group consisting of agarose, deacetylated konjac glucomannan, hydroxylethyl curdlan;

[b] 2 to 95 wt % of one or more denaturing agents;

[c] 0 to 50 wt % of one or more non-gelling additives; and

[d] 0.2 to 6 wt % of one or more electrophoretic buffers;

wherein the gel resulting from the addition of water to 100 wt % to said combination is capable of resolving nucleic acid fragments having at least 50 bases which differ from each other by at least one base.

3. The composition of claim 1 wherein the gelling polysaccharide is agarose.

4. The composition of claim 1 wherein the gelling polysaccharide is deacetylated konjac glucomannan.

5. The composition of claim 1 wherein the gelling polysaccharide is hydroxyethyl curdlan.

6. The composition of claim 1 wherein the gelling polysaccharide is agarose extracted from the *Pterocladia* species of seaweed.

7. The composition of claim 1 wherein the denaturing agent is: urea; biuret; $C_{1-6}$ alkyl urea; dimethylsulfoxide; $C_{1-6}$ monoaldehyde; $C_{1-6}$ dialdehyde; formamide; $C_{1-6}$ alkyl formamide; dimethylsulfoxide; pyrrolidinone; $C_{1-6}$ alkyl pyrrolidinone; $C_{2-4}$ glycol; or a mixture thereof.

8. The composition of claim 1 wherein the denaturing agent is: urea; formamide; dimethylformamide; dimethylsulfoxide; or a mixture thereof.

9. The composition of claim 1 wherein the denaturing agent is: urea; formamide; dimethylformamide; or a mixture thereof.

10. The composition of claim 1 wherein the denaturing agent is urea.

11. The composition of claim 1 wherein the non-gelling additive is present and is: glycerol; $C_{1-4}$ glycol; $C_{1-4}$ polyglycol; dextran; locust bean gum; depolymerized agarose; or a mixture thereof.

12. The composition of claim 1 wherein the non-gelling additive is present and is: glycerol, ethylene glycol, erythritol, locust bean gum; or a mixture thereof.

13. The composition of claim 1 wherein the non-gelling additive is present and is: glycerol; ethylene glycol; or a mixture thereof.

14. The composition of claim 1 wherein the electrophoretic buffer is a biological buffer and is tris-R-EDTA where R is: borate; phosphate; taurine; acetate; carbonate; or glycine; or a mixture of such buffers.

15. The composition of claim 1 wherein the electrophoretic buffer is a biological buffer and is tris-R-EDTA where R is: borate; phosphate; taurine; or acetate; or a mixture of such buffers.

16. The composition of claim 1 wherein the electrophoretic buffer is tris-borate-EDTA.

17. The composition of claim 1 wherein:

(i) the gelling polysaccharide is agarose, konjac glucomannan, hydroxyethyl curdlan, or a mixture thereof;

(ii) the denaturing agent is: urea; biuret; $C_{1-6}$ alkyl urea; dimethylsulfoxide; $C_{1-6}$ monoaldehyde; $C_{1-6}$ dialdehyde; formamide; $C_{1-6}$ alkyl formamide; pyrrolidinone; $C_{1-6}$ alkyl pyrrolidinone; $C_{2-4}$ glycol; or a mixture thereof; and (iii) the electrophoretic buffer is a biological buffer and is tris-R-EDTA where R is: borate; phosphate; taurine; acetate; carbonate; or glycine; or a mixture of such buffers.

18. The composition of claim 17 wherein:

(iv) the non-gelling additive is present and is: glycerol; $C_{1-4}$ glycol; $C_{1-4}$ polyglycol; dextran; locust bean gum; depolymerized agarose; or a mixture thereof.

19. The composition of claim 1 wherein:

(i) the gelling polysaccharide is agarose, hydroxyethyl curdlan, deacetylated konjac glucomannan, or a mixture thereof;

(ii) the denaturing agent is: urea; formamide; dimethylformamide; dimethylsulfoxide; or a mixture thereof; and (iii) the electrophoretic buffer is a biological buffer and is tris-R-EDTA where R is: borate; phosphate; taurine; or acetate; or a mixture of such buffers.

20. The composition of claim 19 wherein:

(iv) the non-gelling additive is present and is: glycerol, ethylene glycol, erythritol, locust bean gum; or a mixture thereof.

21. The composition of claim 1 wherein:

(i) the gelling polysaccharide is agarose extracted from the *Pterocladia* species of seaweed;

(ii) the denaturing agent is urea; and the electrophoretic buffer is tris-borate-EDTA.

22. The composition of claim 21 wherein:

(iv) the non-gelling additive is present and is: glycerol; ethylene glycol; or a mixture thereof.

23. The composition of claim 1 wherein the ingredients are present in the amounts:

(a) gelling polysaccharide: 2 to 8 wt %;

(b) denaturing agent: 10 to 70 wt %; and (d) electrophoretic buffer: 0.3 to 5 wt %.

24. The composition of claim 23 wherein the non-gelling additive is present in the amount 2 to 30 wt %.

25. The composition of claim 1 wherein the ingredients are present in the amounts:

(a) gelling polysaccharide: 3 to 6 wt %;

(b) denaturing agent: 12 to 60 wt %; and (d) electrophoretic buffer: 0.4 to 4 wt %.

26. The composition of claim 23 wherein the non-gelling additive is present in the amount 5 to 20 wt %.

* * * * *